United States Patent [19]

Nason

[11] Patent Number: 4,610,171

[45] Date of Patent: Sep. 9, 1986

[54] URINANALYSIS VIAL

[76] Inventor: Frederic L. Nason, 6830 Orion Ave., Van Nuys, Calif. 91406

[21] Appl. No.: 727,727

[22] Filed: Apr. 26, 1985

[51] Int. Cl.$^4$ ............................................. G01N 1/14
[52] U.S. Cl. .............................. 73/864.62; 73/864.73; 73/864.91; 422/102; 422/100
[58] Field of Search ........... 73/864.62, 864.91, 864.73; 128/767, 763, 765; 422/102, 100

[56] References Cited

U.S. PATENT DOCUMENTS

| | | | |
|---|---|---|---|
| 3,013,557 | 12/1961 | Pallotta | 128/765 |
| 3,203,247 | 8/1965 | Bicek | 73/864.91 |
| 3,319,622 | 5/1967 | Shiner | 73/864.73 X |
| 3,411,343 | 11/1968 | Baird, Jr. | 73/864.91 X |
| 3,460,529 | 8/1969 | Leucci | 73/864.62 X |
| 3,610,048 | 10/1971 | Weeks | 73/864.73 X |
| 3,718,133 | 2/1973 | Perry et al. | 73/864.91 X |
| 3,838,970 | 10/1974 | Kline | 422/102 X |
| 3,938,961 | 2/1976 | Lanier | 73/864.91 X |
| 4,064,760 | 12/1977 | Benjamin | 73/864.91 X |
| 4,221,225 | 9/1980 | Sloan | 73/864.62 X |
| 4,338,826 | 7/1982 | Jacoby et al. | 73/864.62 |
| 4,463,616 | 8/1984 | Blecher | 73/864.91 X |

FOREIGN PATENT DOCUMENTS

| | | | |
|---|---|---|---|
| 13387 | 2/1977 | Japan | 73/864.62 |
| 572614 | 2/1976 | Switzerland | 73/864.62 |
| 1478620 | 7/1977 | United Kingdom | 73/864.91 |
| 491867 | 11/1975 | U.S.S.R. | 73/864.62 |

OTHER PUBLICATIONS

"Gas Sampler for Chromotography"; Ind. Lab. (USA), vol. 44, No. 6; Dec. 1978; pp. 769-770; L. A. Frangulyan et al.

Primary Examiner—Stewart J. Levy
Assistant Examiner—Tom Noland
Attorney, Agent, or Firm—Kelly, Bauersfeld & Lowry

[57] ABSTRACT

The vial is particularly designed to retrieve urine specimens from a jar or other container provided by a patient. The vial itself is in the form of a bellows biased to its expanded position. A straw is provided axially in the bellows such that the bellows can be manually collapsed and then released so that the specimen is sucked up through the straw into the bellows. The bellows itself has a bottom shaped to be received in a centrifuge and is also provided with a cap which replaces the straw prior to centrifuging. The cap itself can be removed after centrifuging and defines a fixed volume for collecting a given amount of sediment and liquid for ultimate analysis on a slide. The straw serves the dual function of axially supporting the bellows arrangement during collapsing by guiding the bellows walls and also as a conduit or passage for transferring urine into the bellows.

8 Claims, 4 Drawing Figures

URINANALYSIS VIAL

FIELD OF THE INVENTION

This invention relates generally to the analysis of liquid specimens and more particularly to an improved urinanalysis vial for facilitating the analysis of urine specimens.

BACKGROUND OF THE INVENTION

In a routine urinanalysis, a urine specimen from a jar or the like provided by a patient is transferred into a test tube or other enclosure for transport to a laboratory. When the specimen arrives at the laboratory, a second transfer of a given quantity of the urine is made to a centrifuge tube, designed to be held in a centrifuge machine. After centrifuging, sediment collected at the extended end of the tube is then in turn analyzed as by visual inspection as well as by placing given volumes on a microscope slide.

The foregoing involves much handling of various tubes and enclosures as well as transfer of the urine specimen itself, all deleterious to sterile conditions.

Improvements in urinanalysis have been effected by provision of multi-purpose tube structures wherein the same tube that is used to transport a urine specimen or other liquid specimen from a doctor's office or hospital to a laboratory is also usable as a centrifuge tube so that no transfer is necessary in carrying out the centrifuging step. In addition, it has been proposed to provide a cap structure on a centrifuge tube which will collect liquid and sediment in a known amount so that a transfer from the cap directly to an examination slide can be effected.

U.S. Pat. No. 3,796,542 illustrates one example of a tube serving several functions. The particular tube illustrated has a helical corrugated wall structure functioning in the manner of a bellows so that liquid specimens can be drawn into the interior of the tube. However, the device in this particular U.S. patent has a syringe structure on its top to be used as a fluid or liquid conduit in passing a specimen into the bellows-like wall structure. This syringe-like passage remains as a part of the overall container. Sediment is removed from the bottom of the container after centrifuging by piercing a membrane.

U.S. Pat. No. 3,460,529 illustrates a sterile device for extracting urine samples and the like wherein there is disclosed the concept of a cap structure for collecting a given amount of sediment for subsequent examination.

BRIEF DESCRIPTION OF THE PRESENT INVENTION

The present invention provides for a urinanalysis vial which can also be used for other liquid or serum specimens capable of performing the same functions as those described in the above U.S. patents, but having additional advantages.

More particularly, the present invention in its broadest aspect constitutes an elongated elastic bellows having a closed bottom and top neck. The bellows is biased to an extended position to define a given volume and is capable of being manually collapsed. A straw is axially positioned in the bellows, an upper portion of the straw being circumferentially frictionally engaged by the neck of the bellows. With this arrangement, manual collapsing of the bellows is axially guided by the straw. The straw itself is frictionally urged through the neck during collapsing but is not completely urged out of the neck. The straw then serves the further function of a passage for transferring a liquid specimen into the bellows upon manual release of the bellows.

After the bellows has been filled, the straw is simply disposed of and a cap is placed on the neck. This cap defines a fixed volume for collection of liquid and sediment after centrifuging of the bellows enclosure. In this latter respect, the bottom of the bellows is shaped to be received directly in a centrifuge machine.

By utilizing a straw, not only for the purpose of stabilizing the collapsing of the bellows arrangement, but also as a passage for transferring the liquid specimen into the bellows, the straw itself can be disposed of and replaced by a cap as described. There is thus avoided the presence of a permanent syringe type passage which can become contaminated and/or contaminate the hands of a user in subsequent manipulation of a container.

BRIEF DESCRIPTION OF THE DRAWINGS

A better understanding of this invention will be had by referring to the accompanying drawings in which.

DETAILED DESCRIPTION OF THE PREFERRED EMBODIMENT

Figure 1:
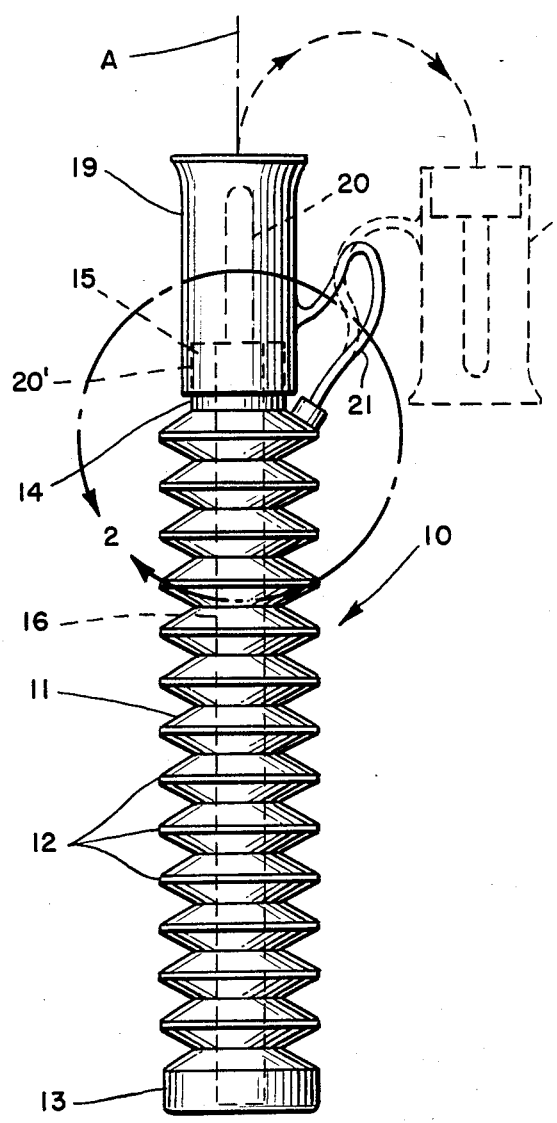
FIG. 1 is a side elevational view of the urinanalysis vial of this invention in expanded position.

Referring first to FIG. 1, there is designated generally by the numeral 10 the urinanalysis vial of this invention for collecting, centrifuging and dispensing urine specimens incidental to laboratory analysis. This vial includes an elongated plastic tube 11 having a corrugated wall 12 normally biased to an expanded position defining a given initial volume. The corrugated wall 12 is capable of being collapsed in the manner of a bellows as will become clearer as the description proceeds.

One end of the tube 11 which is illustrated as the bottom end in FIG. 1, is illustrated at 13 and is shaped to be received and held in a centrifuge machine. The other end of the tube 11 in turn defines a top 14 terminating in a cylindrical collar coaxial with the corrugated wall.

Figure 2:
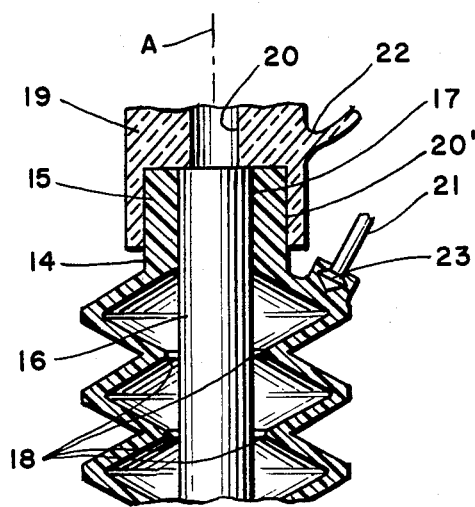
FIG. 2 is an enlarged cross section of a portion of the vial enclosed within the circular arrow 2 of FIG. 1.

With particular reference to the enlarged cross section of FIG. 2, the cylindrical collar is shown at 15.

A straw indicated by the phantom lines at 16 in FIG. 1 is received axially in the tube 11. Referring specifically again to FIG. 2, this straw has an outside diameter substantially equal to the inside diameter of the cylindrical collar 15 so as to be frictionally held in the collar as indicated at 17. The remaining portion of the straw 16 passes axially down the tube.

Still referring to FIG. 2, the corrugations of the tube wall define minimum internal diameters indicated at 18. These internal diameters are related to the diameter of the straw such that when the corrugated wal is collapsed in the manner of the bellows, the exterior wall of the straw will function to hold the corrugations substantially in rectilinear axial alignment.

Figure 3:
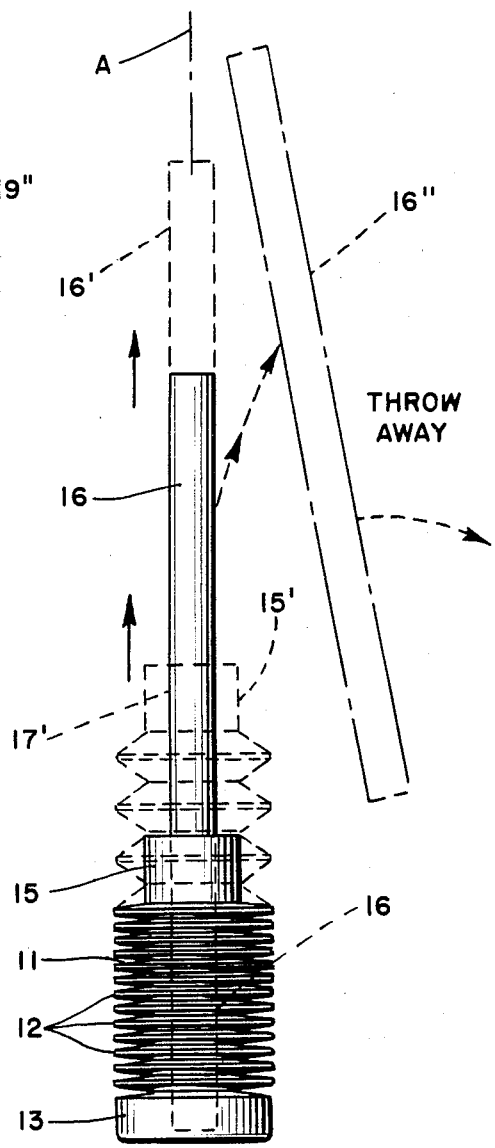
FIG. 3 is a side elevational view of the vial of FIG. 1 in collapsed condition; and, FIG. 4 is a schematic illustration of the cap of the vial and the manner in which a liquid specimen is transferred to a slide.

In both FIGS. 1 and 2 and in FIG. 3, the axis of the plastic tube 11 having the corrugated walls is indicated by the letter A and it can be appreciated that the straw 16 will guide the collapsing of the corrugated wall in a bellows-like manner to a rectilinear path coinciding with the axis A.

Again referring to FIGS. 1 and 2, the assembly is completed by the provision of a cap 19 having an interior hollow portion 20 defined in part by an initial cylindrical entrance 20' fitting over the collar 15 so that the cap is supported on the top of the tube 11. The hollow portion 20 communicates with the cylindrical entrance 20' and extends upwards into the cap to define a fixed volume for the collection of sediment and a given amount of fluid upon centrifuging of a liquid specimen in the tube 11.

The cap 19 itself is preferably temporarily held to the tube 11 as by a tie 21 secured at points 22 and 23 to the cap and the upper end of the tube 11 respectively as best illustrated in FIG. 2.

In operation, the vial would normally be supplied in its expanded position illustrated in FIG. 1 with the cap 20 in place. When a specimen is to be analyzed by the laboratory, the physician or nurse will first remove the cap 19 to an out-of-the-way dotted line position such as indicated at 19" in FIG. 1, the cap still being held captive to the plastic tube 16 so that it can be subsequently replaced.

The physician or nurse can then manually collapse the corrugated wall of the tubes 11 in the manner of a bellows resulting in the urging of the straw 16 frictionally through the neck or collar 15 as illustrated in FIG. 3. In other words, the bottom of the elongated tube 11 pushes the lower end of the straw 16 as collapsing takes place to urge the straw out through the neck or collar portion 15. The exposed end of the straw 16 can then be positioned in a urine sample or other serum or liquid sample to be analyzed, and when the corrugated wall portion of the tube 11 is manually released, the corrugated wall will tend to expand to its initial expanded position illustrated in FIG. 1.

As the wall expands as partially indicated in the phantom lines in FIG. 3, the frictional engagement of the annular collar or neck 15 moves the straw 16 along with the neck so that in the phantom line position illustrated in FIG. 3, when the neck 15 assumes the position 15', the upper end of the straw 16 will assume the position illustrated at 16'.

When the expansion of the corrugated wall is complete to its initial position illustrated in FIG. 1, a fixed volume of fluid specimen will have been drawn into the tube 11. The straw 16 is then simply removed from the neck or collar 15 and disposed of as indicated by the phantom lines 16" in FIG. 3. The cap 19 is then replaced onto the neck or annular collar 15.

Thereafter, the bottom end 13 is held in a centrifuge machine and the specimen within the plastic tube centrifuged so that sediment will collect in the cap 19, specifically within the fixed volume interior 20.

In the preferred embodiment of this invention, the cap 19 is transparent, so that after centrifuging the sediment along with a fixed amount of liquid can be observed visually.

In addition, the cap 19 is preferably pliable so that the contents within the fixed volume 20 in the form of sediment can be squeezed onto a microscope slide after the same have been intermixed.

Figure 4:
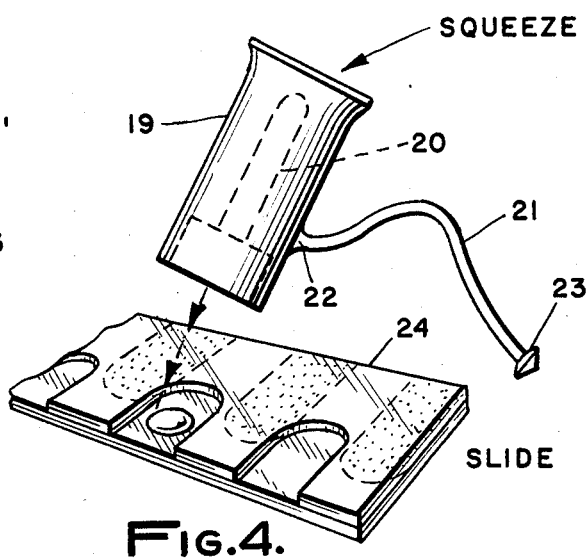

The foregoing is schematically illustrated in FIG. 4 wherein the arrows indicate a squeezing of the top portion of the cap 19 to express the intermixed sediment with a given amount of fluid within the fixed volume 20 onto a slide 24.

From the foregoing, it will be evident that the straw 16 has served a dual function. First, the straw itself structurally holds the collapsing bellows in axial alignment so that manual collapsing of the tube can readily take place without undue bowing out of the structure during the application of collapsing pressure. Second, the extension of the straw 16 as a consequence of the frictional engagement with the collar 15 provides for a convenient and easy passage to effect transfer of a specimen from a jar or other container into the bellows-like tube when the wall corrugations are released manually so that they can expand to the position illustrated in FIG. 1.

By disposing of the straw thereafter, the contaminated straw itself can no longer affect other components.

The cap 19 held captive to the plastic tube is then easily replaceable onto the collar 15 and the subsequent steps of centrifuging and analysis of the sediment can readily be carried out.

When expressing the contents of the cap, the tie can be pulled free of the tube at the connection point 23 by applying an intentional force if desired.

The straw itself is a very inexpensive component of the system, and as a consequence, the overall urinanalysis vial can be very economically manufactured.

While the vial has been described with respect to a urine specimen, it is clear that the vial could be used in the analysis of any serum liquid.

Changes falling within the scope and spirit of this invention will occur to those skilled in the art. The urinanalysis vial is therefore not to be thought of a limited to the specific embodiment set forth for illustrative purposes.

I claim:

1. A vial for liquid specimens including, in combination:
   (a) an elongated elastic bellows having a closed bottom and top neck of generally cylindrical configuration, said bellows being biased to an extended position defining a given volume and capable of being manually collapsed; and
   (b) a straw axially positioned in said bellows, an upper portion of said straw being circumferentially frictionally engaged by said neck, said straw being substantially contained within said bellows when said bellows is in the extended position, whereby said bellows is axially guided by said straw when said bellows is collapsed with said straw thereupon being frictionally urged through said neck such that the upper end of said straw projects substantially from said bellows, said straw further functioning as a passage for transferring a liquid specimen by suction into said bellows upon manual release of the bellows.

2. A vial according to claim 1, in which said straw is disposed of after a specimen has been transferred into said bellows; and a cap receivable over said neck and defining a fixed volume for collection of liquid and sediment.

3. A vial according to claim 2, in which said bottom is shaped to be held in a centrifuge.

4. A urinanalysis vial for collecting, centrifuging and dispensing urine specimens incidental to laboratory analysis, including, in combination:

(a) an elongated plastic tube having a corrugated wall normally biased to an expanded position defining a given initial volume and capable of being axially collapsed in the manner of a bellows, one end of said tube defining a bottom shaped to be received and held in a centrifuge machine and the other end of said tube defining a top terminating in a cylindrical collar coaxial with the corrugated wall;

(b) a straw received axially in said tube having an outside diameter substantially equal to the inside diameter of said cylindrical collar so that the upper end of said straw is frictionally held in said collar, the remaining portion of the straw passing axially down the tube, the corrugations of the wall defining minimum internal diameters being related to the diameter of the straw such that when the corrugated wall is collapsed in the manner of a bellows, the exterior wall of the straw will function to hold the corrugations in substantial rectilinear axial alignment; and (c) a cap having an interior hollow portion defined by a initial cylindrical entrance for fitting over said collar so that the cap is supported on the top of the tube, said hollow portion communicating with said cylindrical entrance and extending up into said cap to define a fixed volume for the collection of sediment and a given amount of fluid upon centrifuging of a liquid specimen in said tube, whereby said cap can be removed and said tube can be manually axially collapsed to cause said straw to be urged frictionally through the collar by the bottom of the tube engaging the straw during the collapsing of the corrugated wall, the extending end of the tube serving as a conduit for sucking a urine specimen into said tube upon manual releasing of the pressure holding the tube in its collapsed state, the tube being filled with a known given volume of specime after the corrugated walls reach their normal expanded position, said straw then being pulled from the collar and disposed of and said cap replaced on the collar, the tube then being in condition for transfer to a centrifuge machine, the liquid specimen being maintained in its sterile condition, said cap again being removable after centrifuging to provide a fixed volume of liquid and sediment for intermixing and dispensing onto an examination slide.

5. A vial according to claim 4, in which said cap is of a transparent material so that said specimen can be visually examined prior to removal from said cap.

6. A vial according to claim 4, in which said cap is of a pliable plastic material so that it can be manually squeezed to facilitate dispensing of said specimen.

7. A vial according to claim 4, including flexible tie means for preventing complete separation of said cap from said tube after removal from the top until an intentional pulling force is applied to the cap to separate the same.

8. A vial for liquid specimens, comprising:

an elongated elastic bellows having a closed bottom and a top defining a generally cylindrical neck, said bellows being normally biased to an extended position and being manually collapsible to a compressed position; and a straw generally coaxially positioned within said bellows with said straw substantially contained within said bellows and with an upper portion of said straw frictionally engaged within said neck when said bellows is in the extended position;

said closed bottom of said bellow pushing said straw partially through said neck upon manual collapse of said bellows whereupon said neck frictionally engages a lower portion of said straw and said straw projects a substantial distance from said bellows;

said bellows being releasable subsequent to collapse to draw a liquid specimen through said straw into the interior of said bellows.

* * * * *